US008354248B2

(12) United States Patent
Hatada et al.

(10) Patent No.: US 8,354,248 B2
(45) Date of Patent: Jan. 15, 2013

(54) PROMOTER-ENCODING DNA FRAGMENT, RECOMBINANT VECTOR, RECOMBINANT TRANSFORMANT, AND USES THEREOF

(75) Inventors: Yuji Hatada, Yokosuka (JP); Yukari Ohta, Yokosuka (JP); Yuko Hidaka, Yokosuka (JP); Nobuyuki Nakamura, Yokosuka (JP)

(73) Assignee: Japan Agency for Marine-Earth Science and Technology, Kanagawa (JP)

( * ) Notice: Subject to any disclaimer, the term of this patent is extended or adjusted under 35 U.S.C. 154(b) by 2 days.

(21) Appl. No.: 12/452,648

(22) PCT Filed: Jul. 9, 2008

(86) PCT No.: PCT/JP2008/062392
§ 371 (c)(1),
(2), (4) Date: Jul. 15, 2010

(87) PCT Pub. No.: WO2009/011259
PCT Pub. Date: Jan. 22, 2009

(65) Prior Publication Data
US 2011/0014677 A1    Jan. 20, 2011

(30) Foreign Application Priority Data

Jul. 13, 2007  (JP) ................................. 2007-183934

(51) Int. Cl.
| | |
|---|---|
| *C12P 21/06* | (2006.01) |
| *C12N 9/00* | (2006.01) |
| *C12N 9/02* | (2006.01) |
| *C12N 9/10* | (2006.01) |
| *C12N 9/88* | (2006.01) |
| *C12N 1/20* | (2006.01) |
| *C12N 15/00* | (2006.01) |
| *C07H 21/04* | (2006.01) |

(52) U.S. Cl. ....... 435/69.1; 435/183; 435/189; 435/193; 435/232; 435/252.3; 435/320.1; 536/23.2

(58) Field of Classification Search ........................ None
See application file for complete search history.

(56) References Cited

U.S. PATENT DOCUMENTS

| | | | |
|---|---|---|---|
| 4,977,089 | A | 12/1990 | Kovacevic |
| 5,559,007 | A | 9/1996 | Suri |
| 2001/0021515 | A1 | 9/2001 | Sato et al. |
| 2004/0166566 | A1 | 8/2004 | Ito et al. |

FOREIGN PATENT DOCUMENTS

| | | |
|---|---|---|
| EP | 0 151 760 | 8/1985 |
| EP | 1 270 730 | 1/2003 |
| JP | 06-217781 | 8/1994 |
| JP | 2000-152784 | 6/2000 |
| JP | 2003-000283 | 1/2003 |
| JP | 2003-052389 | 2/2003 |

OTHER PUBLICATIONS

Accession ABL33157. Mar, 26, 2002.*
Chica et al. Curr Opin Biotechnol. Aug. 2005;16(4):378-84.*
Sen et al. Appl Biochem Biotechnol. Dec. 2007;143(3):212-23.*
Niu et al. "Development of a pair of bifunctional expression vectors for *Escherichia coli* and *Bacillus licheniformis*." Journal of Industrial Microbiology & Biotechnology; Office Journal of the Society for Industrial Microbiology, vol. 34, No. 5, Jan. 26, 2007, pp. 357-362.
Zhang et al. "High-level expression and secretion of methyl parathion hydrolase in *Bacillus subtilis* WB800." Applied and Environmental Microbiology, vol. 71, No. 7, Jul. 2005, pp. 4101-4103.
Takeda et al "Purification and enzymatic properties of a highly alkaline mannanase from alkaliphilic *Bacillus* sp. strain JAMB-750." J. Biol. Macromol., vol. 4, No. 2, 2004, pp. 67-74.
Ohta et al. "Enzymatic properties and nucleotide and amino acid sequences of a thermostable beta-agarase from the novel marine isolate JAMB-A9.", Biosci. Biotechnol. Biochem., 2004, vol. 68, No. 5, pp. 1073-1081.
Hatada et al. "Hyperproduction and application of r-Agarase to enzymatic enhancement of antioxidant activity of porphyran.", J. Agric. Food Chem., 2006, vol. 54, pp. 9895-9900.
J. Biol. Macromol., 2004, vol. 4, No. 2, p. 67-74.

* cited by examiner

*Primary Examiner* — Christian Fronda
(74) *Attorney, Agent, or Firm* — Jacobson Holman, PLLC

(57) ABSTRACT

A DNA fragment containing a gene which encodes a specific gene regulatory region alone or the gene regulatory region together with a signal peptide; a recombinant vector containing the DNA fragment; a transformant containing the recombinant vector; and a method of producing a recombinant protein by using the transformant. According to the invention, it is possible to produce a protein in a large amount at a high efficiency regardless of the kind of the recombinant protein.

17 Claims, No Drawings

PROMOTER-ENCODING DNA FRAGMENT, RECOMBINANT VECTOR, RECOMBIANT TRANSFORMANT, AND USES THEREOF

This is a 371 of PCT/JP08/062392 filed Jul. 9, 2008.

TECHNICAL FIELD

The present invention relates to a DNA fragment comprising a base sequence encoding a signal peptide and a base sequence regulating transcription in the production of a recombinant protein, a recombinant vector comprising the same, a transformant transformed therewith, and the use thereof. As a cross-reference to a related patent application, the present application claims priority under Japanese Patent Application No. 2007-183934 filed on Jul. 13, 2007, the entire contents of which are hereby incorporated by reference.

With advances in genetic engineering in recent years, it has become possible to produce proteins using various organisms as host cells. Host-vector systems, in which a recombinant vector containing a foreign gene is introduced into a host cell, are particularly well known. Using a host-vector system, it is possible to obtain a recombinant protein without incorporating a foreign gene into the chromosome of the host cell.

Escherichia coil (E. coli) is widely employed as a host cell in host-vector systems (for example, see Japanese Patent 2,988,951, as well as other members of this patent family, namely European Patent 0441361 and U.S. Pat. No. 5,304,471 (also referred to hereinafter as Patent Document 1), the entire contents of which are hereby incorporated by reference). E. coli has a short generation period of about 20 minutes and can utilize a variety of sugars to proliferate. A large number of plasmid vectors have been developed that are suited to E. coli. The rapid and stable industrial production of recombinant proteins has been achieved with host-vector systems employing E. coli as host cell.

However, the property of E. coli, whereby recombinant protein accumulates within the bacterium, impedes the growth of E. coli. The action of protease within the bacterium tends to result in the functional loss of recombinant protein, presenting a disadvantage in terms of the large-quantity, stable production of recombinant protein. Further, the cell mass must be recovered and ruptured, and great care must be exercised to remove endothermic substances in the form of lipopolysaccharides to obtain the recombinant protein. Thus, there is a problem in that the steps of collecting and purifying the recombinant protein are complex.

Accordingly, to solve this problem, research has been conducted into host-vector systems employing *Bacillus subtilis* (*B. subtilis*). *B subtilis* has a generation period of 30 minutes—roughly comparable to that of *E. coli*—and is capable of secreting proteins externally. Further, liposaccharides are not contained as structural components of the bacterium. Thus, host-vector systems employing *B. subtilis* are capable of producing larger quantities of recombinant protein in more stable fashion than host-vector systems employing *E. coli*, and afford the advantage of ease of collection and purification of the recombinant protein.

As an example of the production of a recombinant protein using a host-vector system with *B. subtilis* as host, the streptolysin O gene derived from *Streptococcus pyogenes* is introduced into an expression vector and the recombinant vector obtained is used to transform *B. subtilis*. It has been reported that streptolysin O can then be obtained from the culture supernatant (see Japanese Unexamined Patent Publication (KOKAI) Heisei No. 05-184372 (also referred to as Patent Document 2 hereinafter), the entire contents of which are hereby incorporated by reference).

DISCLOSURE OF THE INVENTION

Problem to be Solved by the Invention

However, based on research by the present inventors, there are cases with host-vector systems employing *B. subtilis* where the base sequence regulating transcription on the recombinant vector (referred to as a "gene regulatory region" hereinafter) does not function properly for one reason or another, depending on the type of recombinant protein. It has thus become clear that there is a problem in the form of suppression of the expression of the recombinant protein. Further, it has been found that even when the gene regulatory region does function properly, in cases where a base sequence encoding a signal peptide (referred to as a "signal peptide gene" hereinafter) does not function, or the combination of the gene regulatory region and the signal peptide gene is unsuitable, there is a problem in that the recombinant protein remains within the cell or within the membrane, where it tends to be broken down by proteases and the like.

Accordingly, to solve these problems, the establishment of a host-vector system that permits the expression of a recombinant protein gene to a high degree and the efficient secretion of the protein to the exterior of the cell regardless of the recombinant protein involved has been found necessary to the production of recombinant protein employing *B. subtilis* as host.

Accordingly, the first object of the present invention is to provide a novel means of efficiently producing large quantities of protein, regardless of the type of recombinant protein. More specifically, it is to provide a DNA fragment comprising a gene regulatory region permitting the expression of a recombinant protein in large quantity, regardless of the recombinant protein involved. Additionally, it is to provide a DNA fragment, comprising the combination of a gene regulatory region and a signal peptide gene, that permits the efficient secretion of a recombinant protein outside the cell. Still further, it is to provide a DNA fragment in which a base sequence encoding a recombinant protein (referred to as a "recombinant protein gene" hereinafter) is linked downstream of a gene regulatory region or gene regulatory region and signal peptide gene.

The second object of the present invention is to provide a recombinant vector comprising the above DNA fragment, a transformant that has been transformed with the same, and a method for producing a recombinant protein using the same.

Means of Solving the Problem

As a result of extensive research, the present inventors cloned the gene regulatory region of *Bacillus* sp. JAMB750, depository number FERM AP-20227. With the goal of enhancing the secretion performance of the signal peptide, they designed a new signal peptide. As a result, it was discovered that when the structural gene of a recombinant protein was spliced downstream of a DNA fragment containing these, inserted into a suitable vector, and introduced into *B. subtilis*, it was possible to produce large quantities of the protein that were efficiently secreted outside the cell, irrespective of the type of protein. The present invention was devised on this basis.

That is, the present invention provides a DNA fragment comprising the base sequence of any one of (a) to (c) below, that is capable of promoting the expression of a gene present downstream thereof:

(a) the base sequence of SEQ ID NO. 1 or 2 of the sequence listing;

(b) the base sequence of SEQ ID NO. 1 or 2 of the sequence listing, wherein one or a few of bases have been deleted, substituted, inverted, or added; or (c) a base sequence of DNA capable of hybridizing under stringent conditions with DNA comprised of a base sequence complementary to the base sequence of SEQ ID NO. 1 or 2 of the sequence listing.

The present invention further provides a DNA fragment that comprises the base sequence of any one of (a) to (c) below, promotes the expression of a gene present downstream thereof, and permits the secretion outside the cell of the genetic product of the gene:

(a) a base sequence comprised of the base sequence of SEQ ID NO. 1 or 2 of the sequence listing and a base sequence encoding a signal peptide directly or indirectly linked downstream thereof;

(b) a base sequence, comprised of the base sequence of SEQ ID NO. 1 or 2 of the sequence listing and a base sequence encoding a signal peptide directly or indirectly linked downstream thereof, wherein one or a few of bases have been deleted, substituted, inverted, or added; or (c) a base sequence of DNA capable of hybridizing under stringent conditions with DNA comprised of a base sequence complementary to a base sequence that is comprised of the base sequence of SEQ ID NO. 1 or 2 of the sequence listing and a base sequence encoding a signal peptide directly or indirectly linked downstream thereof.

The present invention further provides a DNA fragment that comprises the base sequence of any one of (a) to (c) below, promotes the expression of a gene present downstream thereof, and permits the secretion outside the cell of the genetic product of the gene:

(a) a base sequence comprised of the base sequence of SEQ ID NO. 1 or 2 of the sequence listing and a base sequence encoding the amino acid sequence of SEQ ID NO. 3 directly or indirectly linked downstream thereof;

(b) a base sequence comprised of the base sequence of SEQ ID NO. 1 or 2 of the sequence listing and a base sequence encoding the amino acid sequence of SEQ ID NO. 3 directly or indirectly linked downstream thereof, wherein one or a few of bases have been deleted, substituted, inverted, or added; or (c) a base sequence of DNA capable of hybridizing under stringent conditions with DNA comprised of a base sequence complementary to a base sequence that is comprised of the base sequence of SEQ ID NO. 1 or 2 of the sequence listing and a base sequence encoding the amino acid sequence of SEQ ID NO. 3 directly or indirectly linked downstream thereof.

The present invention further provides a DNA fragment comprising the base sequence of the DNA fragment of the present invention comprising the above-described gene regulatory region and a base sequence encoding a recombinant protein directly or indirectly linked downstream thereof, and a DNA fragment comprising the base sequence of the above-described DNA fragment of the present invention comprising a gene regulatory region and a peptide gene and a base sequence encoding a recombinant protein directly linked downstream thereof.

The above recombinant protein is desirably an enzyme selected from the group consisting of oxidoreductases, transferases, hydrolases, phosphorylases, lyases, isomerases, ligases/synthetases, and modifying enzymes.

The present invention further provides a recombinant vector comprising the DNA fragment of the present invention.

The above recombinant vector is desirably a plasmid, bacteriophage, or retrotransposon.

The present invention further provides a transformant that comprises the host of (a) or (b) below:

(a) a host transformed with the above-mentioned DNA fragment of the present invention; or (b) a host comprising the above-mentioned recombinant vector of the present invention.

The above host is desirably a microorganism, preferably a gram-positive bacterium, and more preferably a microorganism of the genus *Bacillus*.

The present invention further provides a method for producing a recombinant protein comprising steps (a) and (b):

(a) cultivating the above-mentioned transformant of the present invention; and (b) collecting the recombinant protein.

The recombinant protein is desirably an enzyme selected from the group consisting of oxidoreductases, transferases, hydrolases, phosphorylases, lyases, isomerases, ligases/synthetases, and modifying enzymes.

The present invention further provides the transformant of the present invention for use in the method for producing a recombinant protein of the present invention.

The present invention further provides the use of the above DNA fragment to produce a recombinant protein.

The present invention further provides the use of the above recombinant vector to produce a recombinant protein.

The present invention further provides the use of the above transformant to produce a recombinant protein.

BEST MODES OF CARRYING OUT THE PRESENT INVENTION

Modes of carrying out the present invention are described in detail below.

(A) The DNA Fragment of the Present Invention

The DNA fragment of the present invention includes a DNA fragment comprising a gene regulatory region; a DNA fragment comprising a gene regulatory region and a signal peptide gene directly or indirectly linked downstream thereof; a DNA fragment comprising a gene regulatory region and a recombinant protein directly or indirectly linked downstream thereof; and a DNA fragment comprising a gene regulatory region, a signal peptide gene directly or indirectly linked downstream thereof, and a recombinant protein gene directly linked downstream thereof.

In the present specification, the phrase "promoting the expression of a gene present downstream thereof" means having the effect of enhancing the transcription efficiency of a gene positioned to the 3' end side of a gene regulatory region and promoting the expression of a genetic product.

The DNA fragment comprising a gene regulatory region of the present invention is a DNA fragment comprising the base sequence given by SEQ ID NO: 1 or 2 in the sequence listing. A DNA fragment comprising the base sequence given by SEQ ID NO: 1 can be obtained from the chromosomal DNA of *Bacillus* sp. JAMB750 by the method described in Embodiment 2, for example. Additionally, a DNA fragment comprising the base sequence given in SEQ ID NO: 2 can be obtained by incorporating a random mutation into the base sequence given by SEQ ID NO: 1 by the method described in Embodiment 5, for example.

Additional methods of obtaining the DNA fragment comprising a gene regulatory region of the present invention are, for example, preparation by chemical synthesis, genetic engineering methods, mutation-inducing methods, and other commonly known methods carried out based on the information in the base sequence given by SEQ ID NO: 1 or 2 in the sequence listing.

The DNA fragment comprising a gene regulatory region of the present invention is made to activate transcription of a protein gene present downstream of it and promote the expression of the protein by, for example, incorporating it into an expression vector and transforming a host in the form of *B. subtilis*, or by transformation by direct incorporation into the chromosome of *B. subtilis*.

In the present specification, the range of the term "one or a few of" in the phrase "a base sequence comprising the deletion, substitution, inversion, addition, and/or insertion of one or a few of bases" is not specifically limited. By way of example, it is 1 to 40, desirably 1 to 30, preferably 1 to 20, more preferably 1 to 9, still more preferably 1 to 5, and optimally, about 1 to 3. The phrase "deletion of bases" means the knocking out or elimination of bases in the sequence. The phrase "substitution of bases" means that other bases are substituted for bases in the sequence. The phrase "inversion of bases" means that the positions of two or more adjacent bases are reversed. The phrase "addition of bases" means that bases have been added. And the phrase "insertion of bases" means that an additional base has been inserted between bases in the sequence.

In the present specification, the phrase "hybridizing under stringent conditions" refers to the base sequence of DNA obtained by the colony hybridization method, plaque hybridization method, Southern blot hybridization method, or the like using DNA as probe; an example is the DNA, or the like, that can be identified by washing the filter under conditions of 65° C. with a 0.1 to 2×SSC solution (1×SSC solution is 150 mM sodium chloride, 15 mM sodium citrate) following hybridization at 65° C. conducted in the presence of from 0.7 to 1.0 M of NaCl, using a filter on which DNA derived from a colony or plaque, or a fragment of such DNA, has been immobilized. Hybridization can be conducted according to the methods described in the literature, such as Molecular Cloning: A Laboratory Manual, 2nd Ed., Cold Spring. Harbor Laboratory, Cold Spring Harbor, N.Y., 1989; and Current Protocols in Molecular Biology, Supplement 1 to 38, John Wiley & Sons (1987 to 1997). These documents are hereby incorporated in their entirety by reference.

DNA having at least a certain degree of homology with a DNA base sequence employed as probe is an example of DNA hybridizing under stringent conditions. An example is DNA having 70 or greater, desirably 80 percent or greater, preferably 90 percent or greater, more preferably 93 percent or greater, still more preferably 95 percent or greater, and optimally, 98 percent or greater homology.

In the present specification, the term "signal peptide" means a peptide that attaches to the amino end of the genetic product of a gene present downstream of a base sequence encoding a signal peptide, causing the genetic product to be secreted to the exterior of the cell. The term "causes the genetic product to be secreted to the exterior of the cell," as set forth above, means an effect whereby a signal peptide attaches to the amino end of a genetic product in the form of a recombinant protein, inducing attachment of the recombinant protein to, and passage through, the endoplasmic reticulum membrane, finally resulting in secretion of the recombinant protein to the exterior of the cell.

In the present specification, the phrase "the base sequence given by SEQ ID NO: 1 or 2 of the sequence listing and an item directly or indirectly linked downstream thereof" means the base sequence given by SEQ ID NO: 1 or 2 of the sequence listing and an item linked by about 0 to 1,000 bases to the 3' end side of this base sequence.

The DNA fragment of the present invention comprised of a gene regulation region and a signal peptide gene directly or indirectly linked downstream thereof is a DNA fragment comprising the above gene regulatory region and a signal peptide gene linked by about 0 to 1,000 bases, desirably a DNA fragment comprising the above gene regulatory region and the signal peptide gene given by SEQ ID NO: 3 of the sequence listing linked by about 0 to 100 bases.

The DNA fragment of the present invention comprised of a gene regulation region and a signal peptide gene directly or indirectly linked downstream thereof can be obtained by the method described in Embodiment 3 or 5, for example. Further, a DNA fragment containing a signal peptide gene can be prepared by any of the commonly known methods, such as chemical synthesis, genetic engineering techniques, and mutagenesis, based on commonly known signal peptide genes and the sequence information given in SEQ ID NO: 3 of the sequence listing. Automated synthesis by a chemical synthesis method is possible by application of the phosphoramidite method, for example. The signal peptide given by SEQ ID NO: 3 of the sequence listing was selected by evaluating the recombinant protein productivity of several tens of candidate amino acid sequences designed by statistically processing amino acid sequence information on the amino end side of the group of proteins secreted by bacteria of the genus *Bacillus*. This sequence can also be subjected to one or a few of, desirably one or two, amino acid residue additions, deletions, or substitutions for use.

The DNA fragment of the present invention that is comprised of a gene regulatory region and a signal peptide gene directly or indirectly linked downstream thereof can be, for example, incorporated into an expression vector that is then used to transform a host in the form of *B. Subtilis*, or directly incorporated into the chromosome of *B. subtilis*, to activate transcription of the protein present downstream thereof, promote expression of the protein, and cause the expressed protein to be secreted to the exterior of the bacterium.

The DNA fragment comprised of the gene regulatory region and a recombinant protein gene directly or indirectly linked downstream thereof of the present invention is a DNA fragment comprised of the above gene regulatory region and a recombinant protein gene linked through about 0 to 1,000 bases to the 3' end side thereof.

The DNA fragment comprised of a gene regulatory region, a signal peptide gene directly or indirectly linked downstream thereof, and a recombinant protein gene directly linked downstream thereof of the present invention is a DNA fragment comprised of the above gene regulatory region, a signal peptide gene linked through about 0 to 1,000 bases to the 3' end side thereof, and a recombinant protein gene ligated to the 3' end side thereof. The signal peptide gene is desirably the signal peptide gene given by SEQ ID NO: 3 of the sequence listing.

A specific example of the DNA fragment of the present invention is, as set forth in Embodiment 4, a DNA fragment comprised of the base sequence given by SEQ ID NO: 1 of the sequence listing; a gene encoding the signal peptide given by SEQ ID NO: 3 linked through about 10 base pairs downstream thereof; and a beta-agarase gene directly linked downstream thereof.

The recombinant protein that is the genetic product of the recombinant protein gene contained in the DNA fragment of the present invention is not specifically limited, and can be any of the various industrial enzymes, physiologically active peptides, and the like that are employed in detergents, foods, textiles, feeds, chemicals, medical treatment, diagnosis, and the like. Based on function, industrial enzymes include oxidoreductases, transferases, hydrolases, phosphorylases, lyases, isomerases, ligases/synthetases, and modifying enzymes. More specific examples are the genes of sugar-degrading enzymes such as cellulase and agarase; sugar transferring enzymes such as cyclodextrin synthetase; disaccharide phosphorylases such as maltophosphorylase and trehalosephosphorylase; and sugar-modifying enzymes such as sulfotransferases. The embodiments describe the use of the DNA fragment of the present invention to bring about the large-quantity secretion and production of alpha and beta-agarase, which are sugar-degrading enzymes, and cellulase.

One method of obtaining the DNA fragment of the present invention comprised of a gene regulatory region and a recombinant protein gene directly or indirectly linked downstream thereof, or the DNA fragment comprised of a gene regulatory region, a signal peptide gene directly or indirectly linked downstream thereof, and recombinant protein gene directly linked downstream thereof, as set forth in Embodiments 3 and 5, is to insert a DNA fragment, comprised of a gene regulatory region and a signal peptide gene directly or indirectly linked downstream thereof, at a multicloning site in the form of the EcoRI site with an *E. coli-B. subtilis* shuttle vector in the form of the plasmid pHY300PLK, and similarly to insert a recombinant protein gene at a multicloning site in the form of the BamHI site, to obtain plasmid DNA.

As a specific example, the chromosomal DNA of an organism having a targeted recombinant protein gene is employed as template in PCR amplification to amplify a recombinant protein gene comprising a base sequence encoding an amino acid sequence containing a site required for stabilizing or activating the secretion of the target protein. The PCR amplification product of the recombinant protein gene obtained and pHY300PLK are digested with the restriction enzyme BamHI to obtain DNA fragments that are then ligated. The ligation reaction solution obtained is used to transform *E. coli*. Those transformants containing the plasmid in which the recombinant protein gene has been inserted at the BamHI site of pHY300PLK are selected. Plasmid DNA is prepared from the transformants. The plasmid DNA obtained is cleaved by treatment with the restriction enzyme EcoRI. The gene regulatory region containing a promoter site, SD sequence, or the like is amplified by PCR employing chromosomal DNA of *Bacillus* sp. JAMB750 as template and ligated with the open-circular plasmid DNA cleaved with EcoRI as set forth above. The ligation reaction solution obtained is then used to transform *E. coli*. Those transformants that have been properly transformed are selected and plasmid DNA is prepared to obtain the DNA fragment of the present invention.

Expression of a recombinant protein gene can be promoted by incorporating the DNA fragment comprising a gene regulatory region and a recombinant protein gene directly or indirectly linked downstream thereof into an expression vector and transforming a host in the form of *B. subtilis*, or through transformation by direct incorporation into the chromosome of *B. subtilis*.

The expression of a recombinant protein can be promoted and the recombinant protein being expressed can be caused to be secreted to the exterior of the bacterium by incorporating the DNA fragment of the present invention comprised of a gene regulatory region, a signal peptide gene directly or indirectly linked downstream thereof, and a recombinant protein gene directly linked downstream thereof into an expression vector and transforming a host in the form of *B. subtilis*, or by transformation by direct incorporation into the chromosome of *B. subtilis*.

(B) The Recombinant Vector of the Present Invention

The DNA fragment of the present invention can be employed by insertion into a suitable vector. The type of vector employed in the present invention is not specifically limited. For example, it can be one that can be self-replicated within the host cell (such as a plasmid), or one that is incorporated into the genome of the host cell in the course of introduction into the host cell and replicated along with the chromosome into which it has been incorporated. The vector employed in the present invention is desirably a plasmid, bacteriophage, or retrotransposon. The DNA fragment of the present invention into which such a vector has been incorporated is functionally and structurally retained within the vector in stable fashion.

Specific examples of vectors that can be self-replicated within the host cell are YCp-type *E. coli*—yeast shuttle vectors such as pRS413, pRS415, pRS416, YCp50, pAUR112, and pAUR123; YIp-type *E. coli*—yeast shuttle vectors such as pRS403, pRS404, pRS405, pRS406, pAUR101, and pAUR135; and *E. coli*-derived plasmids (such as ColE-based plasmids such as pBR322, pBR325, pUC18, pUC19, pUC119, pTV118N, pTV119N, pBluescript, pHSG298, pHSG396, and pTrc99A; p1A-based plasmids such as pACYC177 and pACYC184; and pSC101-based plasmids such as pMW118, pMW119, pMW218, and pMW219); *B. subtilis*-derived plasmids (such as pUB110 and pTP5); and *E. coli-B. subtilis* shuttle vectors such as pHY300PLK. Examples of phage vectors are lambda phages (such as Charon 4A, Charon 21A, EMBL4, lambdagt100, gt11, and zap); phiX174, M13mp18, and M13mp19. An example of a retrotransposon is Ty factor. Expression vectors such as the pGEX series (made by Pharmacia) and the pMAL series (made by Biolabs) can be employed as the expression vector expressing a fused protein.

In addition to the DNA fragment of the present invention, it is possible to functionally incorporate selection marker genes, terminators, enhancers, and the like into the recombinant vector of the present invention. Examples of selection marker genes are genes for which complements are lacking in the host cell, such as the dihydrofolate reductase (DHFR) gene and the *Schizosaccharomyces pombe* gene TPI, as well as genes imparting resistance to drugs such as ampicillin, kanamycin, tetracycline, chloramphenicol, cycloheximide, tetramycin, neomycin, and hydromycin. The methods used to functionally link the DNA fragment of the present invention, selection marker genes, terminators, and enhancers and insert them into a suitable vector are well known to persons having ordinary skill in the art. Examples are the methods described in Molecular Cloning (1989) (Cold Spring Harbor Lab.), which is hereby incorporated in its entirety by reference. The insertion positions within the various recombinant vectors may be any region that is not involved in replication of the recombinant vector. Normally, a multicloning site within the vector is employed.

(C) The Transformant of the Present Invention

The DNA fragment or recombinant vector of the present invention can be inserted into a suitable host to prepare a transformant. That is, the transformant of the present invention is one into which the DNA fragment of the present invention is introduced or that contains the recombinant vector of the present invention.

In the present specification, the phrase "into which a DNA fragment is introduced" within the phrase "host into which a DNA fragment is introduced" means that a bacteriophage or the like is used to introduce the DNA fragment of the present invention into a host cell, or that the DNA fragment of the present invention is incorporated into the chromosomal DNA of a host cell.

The host cell into which the DNA fragment or recombinant vector of the present invention is introduced is a microorganism, desirably a gram-positive bacterium, preferably *B. subtilis*, and optimally strain ISW1214, BD170, or 168 of *B. subtilis*. However, any bacterium of the genus *Bacillus* other than *B. subtilis* that is capable of stably retaining and replicating the DNA fragment or recombinant vector of the present invention can be employed.

In the present specification, the term "genus *Bacillus*" covers all the generally known strains contained in the genus *Bacillus* without limitation. For example, it means: *Bacillus subtilis, Bacillus licheniformis, Bacillus lentus, Bacillus stearothermophilus, Bacillus alkalophilus, Bacillus amyloliquefaciens, Bacillus cereus, Bacillus pumilus, Bacillus clausii, Bacillus halodurans, Bacillus megaterium, Bacillus coagulans, Bacillus circulans,* and *Bacillus thuringiensis*. Reclassification into the genus *Bacillus* is ongoing, and strains that have been reclassified within this genus are also included. For example, the genera *Geobacillus, Alkalibacillus, Amphibacillus, Amylobacillus, Anoxybacillus, Goribacillus, Cerasibacillus, Gracilibacillus, Halolactibacillus, Halalkalibacillus, Filobacillus, Jeotgalibacillus, Salibacillus, Oceanobacillus, Marinibacillus, Lysinibacillus, Lentibacillus, Ureibacillus, Salinibacillus, Pontibacillus, Piscibacillus, Paraliobacillus, Virgibacillus, Salsuginibacillus, Tenuibacillus, Thalassobacillus, Thermalkalibacillus,* and *Tumebacillus* exist. These are also included within the genus *Bacillus* in the present specification.

The method of incorporating the DNA fragment or recombinant vector of the present invention into a host cell is not specifically limited. For example, the competent cell method, protoplast method, electroporation method, calcium ion method, lipofection method, spheroblast method, lithium acetate method, transformation method, transfection method, or homologous or heterogenous recombination method can be employed. When the host cell is *B. subtilis*, the competent cell method or protoplast method is desirable.

By way of example, a transformant that has been transformed by the DNA fragment or recombinant vector of the present invention can be obtained by a method employing the expression of a suitable gene such as a selection marker gene spliced downstream of the DNA fragment of the present invention as an index; by a method based on hybridization employing a DNA probe; or by a method utilizing the substrate specificity of a recombinant protein. A specific example of a method utilizing the substrate specificity of recombinant protein, as set forth in Embodiment 4, is to incorporate a beta-agarose gene downstream of the DNA fragment of the present invention, cultivate on agar medium host cells that have been subjected to the transformation operation, and select those colonies where the agar is dissolved by agarose activity to obtain a transformant that has been transformed by the DNA fragment or recombinant vector of the present invention.

(D) The Method for Producing a Recombinant Protein of the Present Invention

The present invention includes a method for producing a recombinant protein by inoculating and culturing the transformant of the present invention by commonly known methods on a suitable medium, and collecting recombinant protein from the culture product.

The nutrient medium employed to culture the transformant of the present invention may be either an agar medium or synthetic medium so long as it contains a carbon source, nitrogen source, inorganic material, and, as needed, suitable quantities of trace nutrients required by the bacterial strain employed.

The carbon source of the nutrient medium employed to culture the transformant of the present invention need only be one that can be utilized by the particular transformant. For example, sugars such as glucose, maltose, lactose, mannose, trehalose, sucrose, mannitol, sorbitol, starch, dextrin, and molasses; organic acids such as citric acid and succinic acid; and fatty acids such as glycerin may be employed.

The nitrogen source of the nutrient medium employed to culture the transformant of the present invention can be various organic and inorganic nitrogen compounds. The medium may also contain various inorganic salts. For example, organic nitrogen sources such as corn steep liquor, soybean dregs, and various peptones; inorganic nitrogen sources such as ammonium chloride, ammonium sulfate, urea, ammonium nitrate, sodium nitrate, and ammonium phosphate; and other compounds can be employed. Amino acids such as glutamic acid and organic nitrogen sources such as urea can double as carbon sources. Still further, natural nitrogen-containing materials such as peptones, polypeptones, bactopeptones, meat extract, fish extract, yeast extract, corn steep liquor, soybean powder, soybean dregs, dried yeast, casamino acids, and soluble vegetable proteins can also be employed as nitrogen sources.

Inorganic materials such as calcium salts, magnesium salts, potassium salts, sodium salts, phosphates, manganese salts, zinc salts, iron salts, copper salts, molybdenum salts, and cobalt salts can be suitably employed. Specific examples are potassium dihydrogenphosphate, magnesium sulfate, ferrous sulfate, manganese sulfate, zinc sulfate, sodium chloride, potassium chloride, and calcium chloride. Further, as needed, amino acids, biotin, thiamin, and other trace nutrient vitamins and the like can be suitably employed.

For example, when preparing a recombinant protein with recombinant *B. subtilis* strain 168, a medium can be employed that is a blend of a carbon source in the form of a monosaccharide such as glucose or fructose, a disaccharide such as sucrose or maltose, or a polysaccharide such as a starch; a nitrogen source in the form of a peptone, soybean powder, yeast extract, meat extract; or corn steep liquor; and a metal salt or the like.

A liquid culturing method is adequate as the culturing method; any from among batch culturing, fed-batch culturing, continuous culturing, and perfusion culturing can be employed. However, from an industrial perspective, a ventilated and stirred culturing method is desirable. The culturing temperature and pH can be suitably selected to create optimal conditions for proliferation of the transformant employed. The culture period need only be greater than or equal to the time required for the microorganism to begin to proliferate; 8 to 120 hours are desirable, and a period allowing maximum production of the genetic product of the recombinant protein gene is preferred. For example, the culturing of a transformant in the form of *B. subtilis* is normally conducted with shaking or ventilation and stirring under conditions selected from among a temperature of from 15 to 42° C., desirably from 28 to 37° C.; a pH of 5 to 9, desirably 6 to 8; and a culturing period of from 2 to 7 days. The method used to confirm the propagation of *B. subtilis* is not specifically limited. For example, the cultured product can be collected and observed under a microscope, or the absorbance thereof can be observed. The concentration of dissolved oxygen in the culture solution is not specifically limited; normally, 0.5 to 20 ppm is desirable. To that end, the level of ventilation, can be regulated, stirring can be conducted, and oxygen can be added by means of ventilation.

When a selection marker is incorporated into the recombinant vector, during culturing of the transformant of the present invention, an antibiotic corresponding to the selection marker can be added in addition to the nutrient medium. For example, when selection markers in the form of genes imparting resistance to tetracycline and chloramphenicol are incorporated, a tetracycline solution and a chloramphenicol solution that have been prepared to suitable concentrations are added. As needed, an expression-inducing agent inducing expression of the gene having the polynucleotides of the present invention is added during culturing or once proliferation of the transformant has been confirmed following the start of culturing. For example, an expression-inducing agent in the form of isopropyl-beta-D-thiogalactopyranosid (IPTG) is employed.

The recombinant protein is collected from the culture product thus obtained. The recombinant protein normally accumulates outside the transformant. Accordingly, the recombinant protein that has accumulated outside the transformant is collected from the culture supernatant. The step of collecting the recombinant protein in the method for producing a recombinant protein of the present invention can be based on common means of collecting proteins. For example, the transformant can be removed by commonly known means and the culture supernatant employed as a recombinant protein-containing product.

However, depending on the type of host, the recombinant protein may sometimes accumulate within the transformant or within the cellular membrane of the transformant. In such cases, by way of example and not by way of limitation, a ruptured cell product obtained from the transformant by breaking down the transformant with an organic solvent or with an enzyme such as lysozyme, ultrasonic rupturing, the French press method, rupturing with glass beads, rupturing in a dyno-mill, or some other cell-rupturing method, and/or the culture product, is separated into transformant and culture supernatant by centrifugal separation, filtration, or some other operation. The culture supernatant thus obtained can be employed as a recombinant protein-containing product. Further, the separated transformant can also be employed as a recombinant protein-containing product.

The recombinant protein-containing product can be employed as is, or, as needed, a concentrated recombinant protein-containing product for industrial application can be prepared by an individual commonly known method, or a combination of such methods, such as salting out, precipitation, dialysis, or ultrafiltration.

For example, the concentrated recombinant protein-containing product can be subjected to a combination of separation and purification by commonly known methods such as ion-exchange chromatography, isoelectric-focusing chromatography, hydrophobic chromatography, gel filtration chromatography, adsorption chromatography, affinity chromatography, reverse-phase chromatography, and the resin column method to obtain a pure recombinant protein.

EMBODIMENTS

Embodiment 1

Constructing a Plasmid for Use as a Gene Regulatory Region Probe

A vector called pPTCF was constructed by the following method for use in probing for gene regulatory region DNA fragments.

PCR was conducted using primer A given by SEQ ID NO: 4 and primer B given by given by SEQ ID NO: 5 in the sequence listing with chromosomal DNA derived from *Microbulbifer* sp. strain JAMB-A7 (Depository No.: FERM BP-8320) as template. This yielded DNA fragment A. The DNA fragment A thus obtained was processed with the restriction enzyme EcoRI and ligated to pHY300PLK (prepared by Yakult), a *B. subtilis-E. coli* shuttle plasmid, that had been processed in advance with EcoRI, to construct circular plasmid B. Circular plasmid B was then used to transform *E. coli* strain HB101, yielding transformant C. Circular plasmids B were prepared from transformant C. One of these, a plasmid comprising a polylinker site derived from PHY300PLK upstream from an agarase gene, was named pPTCF.

Embodiment 2

Obtaining a Gene Regulatory Region (1)

The chromosomal DNA of *Bacillus* sp. strain JAMB750 (Depository No.: FERM AP-20227) was treated with the restriction enzyme Sau3AI. The product was then cleaved with the restriction enzyme BamHI, mixed with the plasmid pPTCF constructed in Embodiment 1, and subjected to a ligation reaction with T4 DNA ligase to obtain a ligation reaction solution D. *B. subtilis* was transformed with ligation reaction solution D to obtain a group of transformants E. The regeneration medium used to culture group of transformants E was DM3 medium comprised of 8 percent sodium succinate, 1 percent agar, 0.5 percent casamino acids, 0.5 percent yeast extract, 0.15 percent potassium dihydrogenphosphate, 0.35 percent dipotassium hydrogenphosphate, 0.5 percent glucose, 0.4 percent magnesium sulfate, 0.01 percent bovine serum albumin, 0.001 percent methionine, 0.001 percent leucine, and 7.5 microgram/mL tetracycline. Transformant group E was cultured on DM3 medium, about 2,000 individual colonies that formed pits in the surrounding agar were selected, and these colonies were liquid cultured. A liquid medium comprised of 3 percent polypeptone S, 0.5 percent fish extract, 0.05 percent yeast extract, 0.1 percent potassium dihydrogenphosphate, 4 percent maltose, 0.02 percent magnesium sulfate, 0.05 percent calcium chloride, and 7.5 microgram/mL tetracycline was employed in liquid culturing under conditions of 30° C. for 48 hours with shaking. The various culture solutions were ultrasonically ruptured (with a Handy sonic model UR-20P made by TOMY SEIKO CO.). The agarase activity of the ultrasonically ruptured products obtained was measured. The transformant with the highest activity was selected. The plasmid of this transformant was named pCDAG1. The agarase activity was measured by the following method.

The agarase activity was measured at 50° C. in a 50 mM MOPS buffer solution (pH 7.0) employing 0.2 percent purified agar (made by Nakalai Tesque) that had been melted by heating to 95° C. and then cooled to 50° C. as substrate. The reduced sugars produced by enzymatic reaction were measured by the 3,5-dinitrosalicylic acid (DNS) method.

Embodiment 3

Obtaining a Gene Regulatory Region (2)

PCR amplification was conducted using primer C given by SEQ ID NO: 6 and primer D given by given by SEQ ID NO: 7 in the sequence listing, with chromosomal DNA derived from *Thalassomonas* sp. strain JAMB-A33 (Depository No.:

DSM 17297) as template. This yielded a DNA fragment F comprised of about 300 bp. PCR-amplified DNA fragment F was processed with the restriction enzyme HindIII, and linked by a ligase reaction to pHY300PLK, which had been cleaved in advance with HindIII, to construct a circular plasmid G. Circular plasmid G was then used to transform *E. coli* strain HB101. Plasmid was prepared from the transformant and named pHYTER.

The expression vector pJEXOPT1 was constructed by the following method.

A gene regulatory region comprised of about 300 bp was amplified by PCR employing primer E given by SEQ ID NO: 8 and primer F given by SEQ ID NO: 9 in the sequence listing with plasmid pCDAG1 obtained in Embodiment 2 as template. This yielded a PCR amplified product H.

Additionally, synthetic single-strand DNA comprised of the base sequence given by SEQ ID NO: 18 and synthetic single-strand DNA comprised of the base sequence given by SEQ ID NO: 19 were annealed to obtain a double-strand DNA fragment I. The ends thereof were subjected to a phosphorylation treatment. The PCR amplification product H obtained and double-strand DNA fragment I were spliced by a ligase reaction. Employing the product as template, PCR amplification was conducted with primer G given by SEQ ID NO: 10 and primer H given by SEQ ID NO: 11. The PCR-amplified product obtained was processed with the restriction enzymes EcoRI and BamHI and then linked with pHYTER that had been processed with EcoRI and BamHI to construct a circular plasmid. This plasmid was employed to transform *E. coli* strain HB101. Plasmid was prepared from the transformant and named pJEXOPT1.

Embodiment 4

Secretion Production of Beta-Agarase with an Expression Vector

A DNA fragment consisting of the beta-agarase gene was amplified by PCR using primer I given by SEQ ID NO: 12 and primer J given by given by SEQ ID NO: 13 in the sequence listing, with chromosomal DNA derived from *Microbulbifer* sp. strain JAMB-A94 (Depository No.: FERM BP-8321) as template. The product was processed with the restriction enzyme BamHI. The expression vector pJEXOPT1 was cleaved with the restriction enzyme BamHI and linked with the beta-agarase gene using ligase. *E. coli* strain HB101 was transformed with pJEXOPT1 containing the beta-agarase gene. A -plasmid was prepared from a transformant exhibiting beta-agarase activity and named pJEXOPT1b. This plasmid was then used to transform *B. subtilis* strain ISW1214. Selection was conducted with a regeneration medium containing tetracycline. The transformants obtained were cultured with stirring at 130 rpm for 72 hours at 30° C. in PPS medium comprised of 5 percent polypeptone S, 0.5 percent fish extract, 0.05 percent yeast extract, 0.1 percent potassium hydrogenphosphate, 5 percent maltose, 0.02 percent magnesium chloride, 0.05 percent calcium chloride, and 15 microgram/mL tetracycline. The bacterial mass was eliminated and the beta-agarase activity of the culture supernatant was measured. As a result, the production of a large quantity of beta-agarase, about 0.15 g per liter of culture solution, was confirmed.

Embodiment 5

Modification of the Gene Regulatory Region

PCR amplification was conducted using phosphorylated primer E given by SEQ ID NO: 8 and phosphorylated primer F given by given by SEQ ID NO: 9 in the sequence listing, with plasmid pCDAG1 as template. The PCR fragment obtained was introduced at the SmaI site of pUC18. Using the plasmid thus constructed as template, random mutations were introduced into the PCR amplified fragment using a Diversify PCR Random Mutagenesis Kit (made by Clontech) with primers E and F according to the kit protocol. The random mutation operation was repeated five times. Employing the PCR product obtained as template, PCR amplification was conducted using primer E and phosphorylated primer F. Subsequently, T4 DNA polymerase was employed to blunt the ends of the PCR product.

Additionally, synthetic single-strand DNA comprised of the base sequence given by SEQ ID NO: 18 and synthetic single-strand DNA comprised the base sequence given by SEQ ID NO: 19 were annealed to obtain a double-strand DNA fragment. The ends of this fragment were subjected to a phosphorylation treatment.

The PCR product and double-strand DNA fragment obtained were spliced by a ligase reaction. The DNA fragment thus obtained was processed with the restriction enzymes EcoRI and BamHI, and then linked with pHYTER that had been processed with EcoRI and BamHI to construct a group of circular plasmids. The group of circular plasmids was employed to transform *E. coli* strain HB101. The roughly several thousand transformants obtained were organized to prepare the plasmid group. This was named plasmid group A. A DNA fragment consisting of the beta-agarase gene was amplified by PCR using primer I given by SEQ ID NO: 12 and primer J given by given by SEQ ID NO: 13, with chromosomal DNA derived from *Microbulbifer* sp. strain JAMB-A94 as template. The product was processed with the restriction enzyme BamHI. Plasmid group A was cleaved with the reaction enzyme BamHI and ligated to the beta-agarase gene with ligase. These plasmids were used to transform *E. coli* strain HB101. Plasmids were prepared from those transformants exhibiting beta-agarase activity. These plasmids were then employed to transform *B. subtilis* strain ISW1214, and selection was conducted with a regeneration medium containing tetracycline. The transformants obtained were cultured with stirring at 130 rpm for 72 hours at 30° C. in PPS medium (5 percent polypeptone S, 0.5 percent fish extract, 0.05 percent yeast extract, 0.1 percent potassium hydrogenphosphate, 5 percent maltose, 0.02 percent magnesium chloride, 0.05 percent calcium chloride, and 15 microgram/mL tetracycline). The beta-agarase activity of the culture supernatants obtained was measured. As a result, a plasmid pJEXOPT2 was obtained that permitted the production of a large quantity of beta-agarase, about 0.2 g per liter of culture solution.

Embodiment 6

Secretion Production of Cellulase with an Expression Vector

A DNA fragment consisting of the cellulase gene was amplified by PCR using primer M given by SEQ ID NO: 14 and primer N given by SEQ ID NO: 15 in the sequence listing with template in the form of the chromosome of *Bacillus akibai* strain 1139 (Depository No.: JCM 9157T) (see J. Gen. Microbiol. 1986, 132, 2329-2335, Fukumori et al., Int J Syst Evol Microbiol. (2005) 55:2309-15, Nogi, Y. et al., which are hereby incorporated in their entirety by reference), a bacterium that produces cellulase. The product was processed with the restriction enzyme BamHI. pJEXOPT1 and pJEXOPT2 were cleaved with the restriction enzyme BamHI and ligated to the cellulase gene with ligase. These products were then used to transform *E. coli* strain HB101. Plasmids were prepared from those transformants that exhibited cellulase activity and named pJEXOPT1C and pJEXOPT2C. These plasmids were used to transform *B. subtilis* strain ISW1214 and selection was conducted with a regeneration medium containing tetracycline. The transformants obtained were cultured with stirring at 130 rpm for 72 hours at 30° C. in PPS medium (3 percent polypeptone S, 0.5 percent fish extract, 0.05 percent yeast extract, 0.1 percent potassium hydrogenphosphate, 4 percent maltose, 0.02 percent magnesium chloride, 0.05 percent calcium chloride, and 15 microgram/mL tetracycline). The cellulase activity of the culture supernatants obtained was measured. As a result, pJEXOPT1C, at about 1 g per liter of culture solution, and pJEXOPT2C, at about 1.5 g, were confirmed to have produced large amounts of cellulase.

Embodiment 7

Secretion Production of Alpha-Agarase with an Expression Vector

A DNA fragment consisting of the alpha-agarase gene was amplified by PCR using primer O given by SEQ ID NO: 16 and primer P given by given by SEQ ID NO: 17 in the sequence listing, with chromosomal DNA derived from *Thalassomonas* sp. strain JAMB-A33 (Depository No.: DSM 17297) as template. The product was processed with the restriction enzyme BamHI. The expression vectors pJEX-OPT1 and pJEXOPT2 were cleaved with the restriction enzyme BamHI and linked with the alpha-agarase structural gene using ligase. These were used to transform *E. coli* strain HB101. Plasmids were prepared from those transformants exhibiting alpha-agarase activity and named pJEXOPT1a and pJEXOPT2a. These plasmids were then used to transform *Bacillus subtilis* strain ISW1214. Selection was conducted with a regeneration medium containing tetracycline. The transformants obtained were cultured with stirring at 130 rpm for 72 hours at 30° C. in PPS medium (5 percent polypeptone S, 0.5 percent fish extract, 0.05 percent yeast extract, 0.1 percent potassium hydrogenphosphate, 5 percent maltose, 0.02 percent magnesium chloride, 0.05 percent calcium chloride, and 15 microgram/mL of tetracycline). The alpha-agarase activity of the culture supernatants obtained was measured. As a result, the production of large quantities of alpha-agarase, 0.2 g per liter of culture solution by pJEXOPT1a and 0.3 g by pJEXOPT2a, was confirmed.

The invention claimed is:

1. An isolated DNA fragment, capable of promoting the expression of a gene downstream thereof, comprising a base sequence selected from the group consisting of base sequence SEQ ID NO: 1, base sequence SEQ ID NO: 1 wherein 1 to 9 bases are deleted, substituted, inverted, or added, a base sequence capable of hybridizing to the complement of SEQ ID NO: 1, wherein the hybridizing is conducted (i) at 65° C. in 0.7-1.0 M NaCl and then (ii) at 65° C. in a 0.1-2×SSC solution, with a 1×SSC solution being 150 mM sodium chloride and 15 mM sodium citrate, and a base sequence sharing at least 95% homology with SEQ ID NO: 1.

2. The isolated DNA fragment according to claim 1 further comprising a base sequence encoding a signal peptide directly or indirectly linked downstream thereof, thereby permitting secretion outside the cell of the genetic product of the gene.

3. The isolated DNA fragment according to claim 1 further comprising a base sequence encoding a signal peptide directly or indirectly linked downstream thereof, thereby permitting secretion outside the cell of the genetic product of the gene, wherein the signal peptide has amino acid sequence SEQ ID NO: 3.

4. The isolated DNA fragment according to claim 1 further comprising the gene regulatory region and a base sequence encoding a recombinant protein directly or indirectly linked downstream thereof.

5. The isolated DNA fragment according to claim 2 further comprising the gene regulatory region and a base sequence encoding a recombinant protein directly or indirectly linked downstream thereof.

6. The isolated DNA fragment according to claim 4 wherein the recombinant protein is an enzyme selected from the group consisting of an oxidoreductase, transferase, hydrolase, phosphorylase, lyase, isomerase, ligase/synthetase, and a modifying enzyme.

7. The isolated DNA fragment according to claim 5 wherein the recombinant protein is an enzyme selected from the group consisting of an oxidoreductase, transferase, hydrolase, phosphorylase, lyase, isomerase, ligase/synthetase, and a modifying enzyme.

8. A recombinant vector comprising the DNA fragment of claim 1.

9. The recombinant vector according to claim 8, wherein the recombinant vector is a plasmid, bacteriophage, or retrotransposon.

10. A transformant selected from the group consisting of
a) a host transformed with the DNA fragment of claim 1 and b) a host comprising a recombinant vector comprising the DNA fragment of claim 1.

11. The transformant according to claim 10, wherein the host is a microorganism.

12. The transformant according to claim 10, wherein the host is a gram-positive bacterium.

13. The transformant according to claim 10, wherein the host is a microorganism of the genus *Bacillus*.

14. A method of producing a recombinant protein comprising the steps of
   a) cultivating the transformant of claim 10 to produce a recombinant protein and
   b) collecting the recombinant protein.

15. The method according to claim 14, wherein the recombinant protein is an enzyme selected from the group consisting of an oxidoreductase, transferase, hydrolase, phosphorylase, lyase, isomerase, ligase/synthetase, and a modifying enzyme.

16. A recombinant vector comprising the DNA fragment of claim 2.

17. The recombinant vector according to claim 16, wherein the recombinant vector is a plasmid, bacteriophage, or retrotransposon.

* * * * *

SEQUENCE LISTING

```
<160> NUMBER OF SEQ ID NOS: 19

<210> SEQ ID NO 1
<211> LENGTH: 355
<212> TYPE: DNA
<213> ORGANISM: Bacillus sp. JAMB750

<400> SEQUENCE: 1
gaattctctt agtgcgcagt ttatccattt tgtgtgatag tacgttatcg cttttcgaac      60
gtgtcaaggg catttgttta tgagattccc ttttgttctg ccaactagtt ggacttattt     120
tttgatgaaa agcacacttg ttaagttatc gtaaaactaa attaattata aaaattaagt     180
tttttaatag atttatatat acaaaaataa agtaattcat ttataatatg taattaaaag     240
cgcttacatt aaagggggac gccctttgcc acaaaggaag tgattgctta cttaataaaa     300
agtaaagtaa aaaagcacat attggtgtaa aaaaagtgca tttaaaggag gatat         355

<210> SEQ ID NO 2
<211> LENGTH: 401
<212> TYPE: DNA
<213> ORGANISM: Artificial Sequence
<220> FEATURE:
<223> OTHER INFORMATION: Mutation of sequence No. 1

<400> SEQUENCE: 2
gaattctctt gtgcgcagtt tatccatttt gtgtgatagt acgttatcgc ttttcgagcg      60
tgtcaagggc atttgtttat gagattccct tttgttctgc caactagttg gacttatttt    120
ttgatgaaaa gcacacttgt taagttatcg taaaactaaa ttaattataa aaattaagtc    180
ttttaataga tttatatatc gcccttgcc acaaaggaag tgattgctta cttatagatt    240
tatatataca aaaataaagt aattcattta taatgtaa ttagaagcgc ttacattaaa     300
gggggcgccc tttgccacaa aggaagtgat tgcttactta ataaaagta aagtaaaaaa     360 gcacatattg gtgtaaaaaa agtgcattta aaggaggata t                        401
```

```
<210> SEQ ID NO 3
<211> LENGTH: 17
<212> TYPE: PRT
<213> ORGANISM: Artificial Sequence
<220> FEATURE:
<223> OTHER INFORMATION: Designated peptide

<400> SEQUENCE: 3

Met Lys Lys Trp Ala Thr Thr Ala Thr Ala Leu Gly Ser Pro Ala Gln
1               5                   10                  15

Ala

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
aagaattcaa ggagcaaagc aatgaaaacc                                    30

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
aggaattctc agttgctcaa cgtaaatttg tc                                 32

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
ttaaagcttc aactttgcac ttacctgacg gaactagc                           38

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
tagaagcttg gtgtaatgtt ttgtaggtga tgccgg                             36

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
ttcgaattct cttagtgcgc agtttatcca ttttgtg                            37

<210> SEQ ID NO 9
<211> LENGTH: 30
<212> TYPE: DNA
<213> ORGANISM: Artificial Sequence
<220> FEATURE:
```

```
<223> OTHER INFORMATION: primer

<400> SEQUENCE: 9
tattttcatc atatcctcct ttaaatgcac                                          30

<210> SEQ ID NO 10
<211> LENGTH: 37
<212> TYPE: DNA
<213> ORGANISM: Artificial Sequence
<220> FEATURE:
<223> OTHER INFORMATION: primer

<400> SEQUENCE: 10
aaagaattct cttagtgcgc agtttatcca ttttgtg                                  37

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
tggggatcca agagcagtgg cagttgttgc cc                                       32

<210> SEQ ID NO 12
<211> LENGTH: 41
<212> TYPE: DNA
<213> ORGANISM: Artificial Sequence
<220> FEATURE:
<223> OTHER INFORMATION: primer

<400> SEQUENCE: 12
aaaggatccc cagcacaagc agcagattgg gatggagttc c                             41

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
ggggatcctt acagcttcac aaagcggatt tc                                       32

<210> SEQ ID NO 14
<211> LENGTH: 42
<212> TYPE: DNA
<213> ORGANISM: Artificial Sequence
<220> FEATURE:
<223> OTHER INFORMATION: primer

<400> SEQUENCE: 14
aaaggatccc cagcacaagc agaaggaaac actcgtgaag ac                            42

<210> SEQ ID NO 15
<211> LENGTH: 32
<212> TYPE: DNA
<213> ORGANISM: Artificial Sequence
<220> FEATURE:
<223> OTHER INFORMATION: primer

<400> SEQUENCE: 15
ttggatcctt actcttcttt ctcttctttc tc                                       32

<210> SEQ ID NO 16
```

-continued

```
<211> LENGTH: 45
<212> TYPE: DNA
<213> ORGANISM: Artificial Sequence
<220> FEATURE:
<223> OTHER INFORMATION: primer

<400> SEQUENCE: 16
aaaggatccc cagcacaagc atcagtaggt gaagaaactg gtaac          45

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17
ttggatccct agtgcgctag ttctaaaata cccc                      34

<210> SEQ ID NO 18
<211> LENGTH: 39
<212> TYPE: DNA
<213> ORGANISM: Artificial Sequence
<220> FEATURE:
<223> OTHER INFORMATION: sequence encoding signal peptide

<400> SEQUENCE: 18
atgaaaaaat gggcaacaac tgccactgct cttggatcc                 39

<210> SEQ ID NO 19
<211> LENGTH: 39
<212> TYPE: DNA
<213> ORGANISM: Artificial Sequence
<220> FEATURE:
<223> OTHER INFORMATION: sequence encoding signal peptide

<400> SEQUENCE: 19
ggatccaaga gcagtggcag ttgttgccca tttttcat                  39
```